United States Patent
Cornu-Artis et al.

(10) Patent No.: US 7,671,017 B2
(45) Date of Patent: Mar. 2, 2010

(54) USE OF A COMBINATION OF CYCLOSPORINE AND PEGYLATED INTERFERON FOR TREATING HEPATITIS C (HCV)

(75) Inventors: Catherine Cornu-Artis, St.Louis (FR); Guylaine Vachon, Basel (CH); Yoko Uryuhara, Kyoto (JP); Kazuo Asakawa, Koganei (JP); Reinhild Elisabeth Mertes, Rheinfelden (DE); Shinsyou Yoshiba, Tokyo (JP)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/572,110

(22) PCT Filed: Jul. 13, 2005

(86) PCT No.: PCT/EP2005/007633

§ 371 (c)(1),
(2), (4) Date: Jan. 11, 2008

(87) PCT Pub. No.: WO2006/005610

PCT Pub. Date: Jan. 19, 2006

(65) Prior Publication Data

US 2008/0138316 A1 Jun. 12, 2008

(30) Foreign Application Priority Data

Jul. 14, 2004 (EP) .................................. 04016583

(51) Int. Cl.
A61K 31/7042 (2006.01)
A61K 38/00 (2006.01)
A61K 38/13 (2006.01)
A61K 38/21 (2006.01)

(52) U.S. Cl. .............................. 514/11; 514/2; 514/19; 514/43; 424/85.4; 424/85.7

(58) Field of Classification Search ....................... None
See application file for complete search history.

(56) References Cited

U.S. PATENT DOCUMENTS

| 5,994,299 | A | 11/1999 | Barriere et al. | |
|---|---|---|---|---|
| 6,524,570 | B1 * | 2/2003 | Glue et al. ................. | 424/85.7 |
| 2002/0013272 | A1 | 1/2002 | Cavanak et al. | |
| 2002/0102279 | A1 | 8/2002 | Chiba et al. | |
| 2003/0216303 | A1 * | 11/2003 | Ambuhl et al. ................. | 514/11 |

FOREIGN PATENT DOCUMENTS

| EP | 0 484 281 | 5/1992 |
|---|---|---|
| WO | 99/62540 | 12/1999 |
| WO | 02/32447 | 4/2002 |
| WO | WO 2005/021028 | 3/2005 |
| WO | 2006/038088 | 4/2006 |
| WO | 2006/071619 | 7/2006 |

OTHER PUBLICATIONS

Brown et al., "Liver transplantation," Current opinion in gastroenterology, vol. 17 No. 3, pp. 299-303 (May 2001).*
Inoue et al., "Combined interferon alpha2b and cyclosporin A in the treatment of chronic hepatitis C: controlled trial.," Journal of Gastroenterology, vol. 38 No. 6, pp. 567-572 (Jun. 2003).*
Kozlowski et al., "Development of pegylated interferons for the treatment of chronic hepatitis C," BioDrugs, vol. 15 No. 7, pp. 419-429 (2001).*
Yoshiba et al., "Interferon and cyclosporin A in the treatment of fulminant viral hepatitis," Journal of Gastroenterology, vol. 30 No. 1, pp. 67-73 (Jan. 1995).*
Tripi et al., "Interferon-alpha Alone versus Interferon-alpha plus Ribavirin in Patients with Chronic Hepatitis C Not Responding to Previous Interferon-alpha Treatment.," BioDrugs, vol. 13 No. 4, pp. 299-304 (Apr. 2000).*
Bizollon T. et al., "Histological Benefit of Retreatment by Pegylated Interferon Alfa-2b and Ribavirin in Patients with Recurrent Hepatitis C Virus Infection Posttransplantation", American Journal of Transplantation, vol. 7, pp. 448-453, (2007).
Cotler, Scott J. et al., "A Pilot Study of the Combinaton of Cyclosporin A and Interferon Alfacon-1 for the Treatment of Hepatitis C in Previous Nonresponder Patients", J Clin Gastroenterol, vol. 36 (4), pp. 352-355, (2003).
Ferenci, P., International Journal of Clinical Practice, vol. 57, No. 7, pp. 610-615, "Peginterferon alfa-2a (40KD) (Pegasys) for the treatment of patients with chronic hepatitis C", Sep. 7, 2003.
Manns, M.P., et al., The Lancet, vol. 358, No. 9286, pp. 958-964, "Peginterferon alfa-2b plus ribavirin compared with interferon alfa-2b plus ribavirin for initial treatment of chronic hepatitis C: a randomised trial", Aug. 2001.

(Continued)

*Primary Examiner*—Zachariah Lucas
(74) *Attorney, Agent, or Firm*—Leslie Fischer

(57) ABSTRACT

A method of treating a patient having a HCV infection which method comprises administering to said patient a cyclosporin A or a cyclosporin A derivative in association with a conjugate of interferon to a water-soluble polymer in an amount effective to alleviate or eliminate one or more of the signs or symptoms of HCV.

16 Claims, No Drawings

OTHER PUBLICATIONS

Manzarbeitia, C., et al., Hepatology, William & Wilkins, vol. 34, No. 4, "40 kDa Peginterferon alfa-2A (PEGASYSs®) as a prophylaxis against hepatitis C infection recurrence after liver transplantation (LT): preliminary results of a randomized multicenter trial", p. 406A, Abstracts AASLD No. 938, Oct. 4, 2001.

Nakagawa, M., et al., Biochemical and Biophysical Research Communications, Academic Press Inc., Orlando, FL, vol. 313, No. 1, pp. 42-47, "Specific inhibition of hepatitis C virus replication by cyclosporin A", Jan. 2, 2004.

International Search Report and written opinion for PCT/EP2005/007633, dated Oct. 19, 2005.

Duncan and Younossi (2003) Cleveland Clinic J. Med. 70:S21-S26.

Shiffman (2004) Cleveland Clinic J. Med. 71:S13-S16.

Papatheodoridis and Cholongitas (2003) J. Viral Hep. 11:287-296.

DaSilva et al, (2002) J. Gastroenterol 37:732-36.

Heathcote et al. (1998) Heptatology 27:11-36-1143.

Package Insert for Intron A, Revision Jul. 2007.

U.S. Appl. No. 10/570,097, filed Dec. 7, 2007, Makoto Hijikata, K. et al.

U.S. Appl. No. 11/720,105, filed May 24, 2007, Kai Lin, W. et al.

U.S. Appl. No. 11/719,684, filed Jan. 29, 2009, Weidmann, B.

U.S. Appl. No. 12/444,941, filed Apr. 9, 2009, Kohjima M. et al.

Inoue et al. "Hepatitis C. virus and cyclosporin A", Igaku no Ayumi, 193(12), pp. 951-954 (2000) Included are copies of the English abstract, the original document in Japanese, and an English translation of the original Japanese document.

Inoue et al. "Antiviral effect of cyclosporin A", Antiviral Development and Therapy Poster Presentation, National Institutes of Health, Jun. 6-9, 1999.

Steinkasserer et al. "Mode of action of SDZ NIUM 811, a nonimmunosupressive cyclosporin A analog with activity against human immunodeficiency virus type 1 (HIV-1): interference with early and late events in HIV-1 replication", Journal of Virology, vol. 69, 814-824 (Feb. 1995).

Watashi, et al. "Cyclosporin A suppresses replication of hepatitis C virus genome in cultured hepatocytes", Hepatology vol. 38, No. 5, 1282-1288 (2003).

EPO, Third Party Observations Under Article 115 EPC, EP 04 764 762.3 (WO 2005/021028) Novartis, Feb. 19, 2007, pp. 1-4.

Retrieved from: http://www3.niad.nih.gov/topics/hepatitisC/prevention.html, 2009, 2 pages [Retrieved on Jun. 27, 2009].

Hansson, 2004, Journal of Bioenergetics and Biomembranes, 36, 407-413.

EPO, Observations by third party pursuant to Art. 115 EPC, Art. 54 EPC. Art. 56 EPC, Art 123(2) EPC, Art. 83 EPC, Art 84 EP, Feb. 8, 2007, pp. 1-6.

Papageorgiou, 1996, Bioorganic and Medicinal Chemistry Letters, 6, 23-26.

Billich, A., et al. "Mode of Action of SDZ NIM 811, a Nonimmunosuppressive Cyclosporin A analog with Activity against Human Immunodeficiency Virus (HIV) Type 1: Interference with HIV Protein-Cyclophilin A Interactions", Journal of Virology, vol. 69, No. 4, pp. 2451-2461 (1995).

Renken, J., Observations under Article 115 EPC,Hoffmann Eitle, Jun. 22, 2007, pp. 2-7.

Watashi, Koichi et al. "Current approaches for developing new anti-HCV agents and analyses of HCV replication using-anti-HCV agents", Biosis, Biosciences Information Service , Philadelphia, PA, US; vol. 55, No. 1, pp. 105-110, Jun. 2005.

Agid et al., "MR diffusion-weighted imaging in a case of West Nile virus encephalitis", Dec. 23, 2003, Neurology, vol. 61., No. 12, pp. 1821-1823.

Ravindra, K. V. et al., "West Nile virus-associated encephalitis in recipients of renal and pancreas transplants . . . ", May 1, 2004, Clinical Infectious Diseases, vol. 38, No. 9, pp. 1257-1260.

Quesniaux, V. F. J. et al, "Cyclophilin binds to the region of cyclosporine involved in its immunosuppressive . . . ", 1987, European Journal of Immunology, vol. 17, No. 9, pp. 1359-1365.

Fukushima et al., "Fasudil hydrochloride hydrate, a rhokinase (ROCK) inhibitor, suppresses collagen production and enhances collagenase activity, in hepatic stellate cells", 2005,Liver International, vol. 25, pp. 829-838.

Fukushima et al., "Hydroxyfasudil, a Rho-kinase (ROCK) inhibitor suppresses cell growth and collagen production in rat hepatic stellate cells"; 2003; Hepatology, vol. 38, No. 4, Suppl. 1, p. 562A.

Nakamuta et al., "Cyclosporine suppresses cell growth and collagen production in hepatic stellate cells", 2005, Transplantation Proceedings, vol. 37, No. 10.

Evers, M. et al., "Synthesis of Non-immunosuppressive Cyclophilin-Binding . . . ", Bioorganic & Medicinal chemistry Letters, 2003, vol. 13, pp. 4415-4419.

\* cited by examiner

USE OF A COMBINATION OF CYCLOSPORINE AND PEGYLATED INTERFERON FOR TREATING HEPATITIS C (HCV)

This application is the National Stage of Application No. PCT/EP2005/007633, filed Jul. 13, 2005, which claims priority to European Application No. 04016583.9, filed Jul. 14, 2004, both of which are hereby incorporated by reference in their entirety.

The present invention relates to the use of a conjugate of interferon to a water-soluble polymer, in particular, pegylated alpha-interferon, in association with a cyclosporin A or a cyclosporine A derivative for the treatment of hepatitis C(HCV).

Several types of interferons, in particular, alfa-interferons are approved for the treatment of chronic HCV, e.g., interferon-alfa-2b (INTRON®), consensus interferon (INFERGEN®), as well as pegylated forms of these and other interferons like pegylated interferon alfa-2a (PEGASYS®) or pegylated interferon alfa-2b (PEG-INTRON®). Said interferons are frequently also used in combination with ribavirin for treatment of HCV infections.

Non-pegylated alfa-interferons exhibit a relatively short half life so that HCV patients normally have to be treated three times weekly. In spite of this dose regimen, an intermittent increase in viral load is observed at days free of drug administration. Pegylated interferons, i.e., interferon derivatives comprising a covalently attached polyethylene glycol (PEG) moiety, exhibit a slower rate of clearance as compared to the corresponding non-pegylated interferon, and a longer half-life. The sustained higher concentrations of pegylated interferons can maintain an almost constant antiviral effect on HCVs and make possible once- or twice-weekly administration. In patients with chronic HCV, a regimen of pegylated interferon alfa-2a, given once weekly, has been shown to be a more effective treatment than a regimen of unpegylated interferon alfa-2a given three times weekly. See *N Engl J Med*, Vol. 343, pp. 1666-1672 (2000).

Cyclosporin A (SANDIMUN®, NEORAL®) is a well-known immunosuppressive agent and particular used for the prevention of transplant rejection, including liver transplant rejection. Cyclosporin A has furthermore been found to suppress the replication of HCV genome in cultured human hepatocytes infected with HCV. See *Hepatology*, Vol. 38, pp. 1282-1288 (2003).

Furthermore, it has been shown in a trial with 120 patients that a combination of cyclosporin A and interferon alfa-2b is significantly more effective in the treatment of chronic HCV than a treatment with interferon alfa-2b alone. See *J Gastroenterol*, Vol. 38, pp. 567-572. (2003). The benefit was mostly achieved in patients with a high viral load and HCV genotype 1.

A pilot study of a combination of cyclosporin A and interferon alfacon-1 in the treatment of HCV genotype 1 infection in previous non-responder patients has also been reported. It did not show the desired effect in that previous non-responders failed to achieve a sustained response to therapy but provided indirect evidence that cyclosporin A may augment the activity of interferon against HCV. See *J Clin Gastroenterol*, Vol. 36, No. 4, pp. 352-355 (2003).

The present invention provides a method of treating a patient having HCV infection, in particular, a chronic form thereof, which method comprises administering to said patient a cyclosporin A or a cyclosporin A derivative in association with a conjugate of interferon to a water-soluble polymer in an amount effective to alleviate or eliminate one or more of the signs or symptoms of HCV, e.g., effective to lower the HCV-RNA measured in a serum sample of a subject, in particular, a human, treated by said method is detectably lowered. The method according to the invention can be of advantage for treating subjects who have not yet received any treatment for HCV or who did not respond to another treatment, e.g., a treatment with interferon alone or with a combination of interferon and ribavirin.

In a further aspect, the invention relates to the use of cyclosporin A or a cyclosporin A derivative in the manufacture of a medicament for the treatment of HCV in association with a conjugate of interferon to a water-soluble polymer, and in yet another aspect to the use of a conjugate of interferon to a water-soluble polymer in the manufacture of a medicament for the treatment of HCV in association with cyclosporin A or a cyclosporin A derivative.

Cyclosporin A and cyclosporin A derivatives are known and described, e.g., in U.S. Pat. No. 4,117,118 or European Patent No. EP 0 539 319. Cyclosporin A derivatives include cyclosporine A prodrugs as described, e.g., in *J Peptide Res*, Vol. 63, pp. 147-154 (2004). Cyclosporin A formulations described, e.g., in EP 0 539 319 or U.S. Pat. No. 5,234,625 form a microemulsion in an aqueous environment, particularly as commercially-available under the tradename NEORAL®.

The pharmaceutical formulations of cyclosporin A or the derivative thereof are preferably a "microemulsion pre-concentrate" as indicated above, the individual components or ingredients of which are pharmaceutically acceptable, e.g., where oral administration is foreseen for oral use.

In addition to the cyclosporin active ingredient, such "microemulsion pre-concentrate" compositions generally comprise:

1) a hydrophilic phase;
2) a lipophilic phase; and
3) a surfactant.

The cyclosporin is carried in the lipophilic phase. Suitably both the hydrophilic and lipophilic phases may serve as carrier medium.

"Microemulsion pre-concentrates" of the invention are of a type providing oil-in-water (o/w) microemulsions. As will be appreciated, however, microemulsion pre-concentrate compositions may contain minor quantities of water or otherwise exhibit fine structural features characteristic of microemulsions, e.g., of o/w or water-in-oil (w/o) type. The term "microemulsion pre-concentrate", as used herein, is accordingly to be understood as embracing such possibilities.

Microemulsions obtained on contacting the "microemulsion pre-concentrate" compositions of the invention with water or other aqueous medium exhibit thermodynamic stability, that is they will remain stable at ambient temperatures, e.g., without clouding or regular emulsion size droplet formation or precipitation, over prolonged periods of time. While the upper limit of dilution with water is not critical, a dilution of 1:1, preferably 1:5 parts per weight ("microemulsion pre-concentrate":$H_2O$) or more will generally be appropriate. Preferably, on contacting with water, the "microemulsion pre-concentrate" compositions provide microemulsions having an average particle size of less than about 1,500 angstroms (Å), more preferably of less than about 1,000 Å or 1,100 Å, e.g., down to about 150 Å or 200 Å.

Conjugates of interferon to a water-soluble polymer are meant to include especially conjugates to polyalkylene oxide homopolymers, such as PEG or polypropylene glycols, polyoxyethylenated polyols, copolymers thereof and block copolymers thereof. As an alternative to polyalkylene oxide-based polymers, effectively non-antigenic materials, such as dextran, polyvinyl pyrrolidones, polyacrylamides, polyvinyl alcohols, carbohydrate-based polymers and the like can be used. Such interferon polymer conjugates are described in U.S. Pat. Nos. 4,766,106 and 4,917,888, European Patent Nos. EP 0 236 987 and EP 0 510 356 and International Publication No. WO 95/13090. Since the polymeric modification sufficiently reduces antigenic responses, the foreign interferon need not be completely autologous. Interferon used to prepare polymer conjugates may be prepared from a mammalian extract, such as human, ruminant or bovine interferon, or recombinantly produced. Preferred are conjugates of interferon to PEG, also known as pegylated interferons.

Especially preferred conjugates of interferon are pegylated alfa-interferons, e.g., pegylated interferon alfa-2a, pegylated interferon alfa-2b, pegylated consensus interferon or pegylated purified interferon alfa product. Pegylated interferon alfa-2a is described, e.g., in European Patent No. EP 0 593 868 and commercially-available, e.g., under the tradename PEGASYS® (Hoffmann-La Roche). Pegylated interferon alfa-2b is described, e.g., in European Patent No. EP 0 975 369 and commercially-available, e.g., under the tradename PEG-INTRON A® (Schering Plough). Pegylated consensus interferon is described in WO 96/11953. The preferred pegylated alfa interferons are pegylated interferon alfa-2a and pegylated interferon alfa-2b. Also preferred is pegylated consensus interferon.

The conjugate of interferon to a water-soluble polymer may be used in form of a composition comprising additional components selected from among those commonly employed with interferons and other antiproliferative or antiviral agents and which are known to those skilled in the art. Conventional pharmaceutical compositions comprising a therapeutically effective amount of interferon together with pharmaceutically acceptable carriers, adjuvants, diluents, preservatives and/or solubilizers may be used in the practice of the invention. Pharmaceutical compositions of interferon include diluents of various buffers, e.g., Tris-HCl, acetate and phosphate, having a range of pH and ionic strength; carriers. e.g., human serum albumin; solubilizers, e.g., tween and polysorbate; and preservatives, e.g., thimerosol and benzyl alcohol. Pharmaceutical composition of interferon are commercially-available as injectable solutions and as lyophilized powders which are reconstituted in an appropriate diluent prior to injection.

It is also within the scope of the present invention to use instead of the conjugate of interferon as described hereinabove a combination, such as a conjugate and ribavirin, in particular, a combination of a pegylated interferon alfa and ribavirin.

The term "in association with", as used herein, in reference to administration of cyclosporin A or a cyclosporin A derivative with a pegylated interferon means that the pegylated interferon is administered prior to, concurrently with, or after administration of the cyclosporin A or a cyclosporin A derivative. Both pharmaceutically active agents may be administered in any suitable way, e.g., orally or parenterally, e.g., IM, IP, SC or IV. Cyclosporin A infusion concentrates are described, e.g., in *Res Disclosure*, Vol. 211, p. 420 (1981). Cyclosporin A or a cyclosporin A derivative are preferably administered orally, e.g., in form of a capsule or an oral solution, whereas the pegylated interferon is preferably administered parenterally, in particular, intravenous (i.v.), intramuscular (i.m.) or subcutaneous (s.c.).

Suitable dosages for practicing the present invention depend on the type of cyclosporine derivative or pegylated interferon employed and on whether the interferon is used in combination with ribavirin. Furthermore the dosage may depend, e.g., on the host, the mode of administration or the severity of the condition treated and on other conditions known to a person skilled in the art. Typically, the cyclosporin A or its derivative are administered in single or, preferably, divided doses, in particular, two to four doses per day, resulting in a total of, e.g., from 2-15 mg/kg/day or about 50-1,000 mg, preferably 50-200 mg per day. The pegylated interferons, are typically administered parenterally one to three times per week, preferably once or twice a week. The total weekly dose ranges, e.g., from about 0.5 mcg/kg/week to about 1 mcg/kg/week in case of pegylated interferon alfa-2b, and is independent from the body weight of the host typically about 180 mcg/week in case of interferon alfa-2a. In combination with ribavirin, a standard dosage of interferon alfa-2b is about 1.5 mcg/kg/week or about 180 mcg/week interferon alfa-2a, respectively and about 600-1200 mg/day, in particular, 800-1,200 mg/day of oral ribavirin.

Preferably, the cyclosporin A or a cyclosporine A derivative and pegylated interferon may be administered over a time period sufficient to lower the HVC-RNA in the serum of a subject in need of such treatment detectably. The usual duration of the treatment is at least 4 weeks, preferably 12 weeks or longer, e.g., from about 20 weeks to about 100 weeks, preferably for a period ranging from about 24 weeks to about 72 weeks, even more preferably from about 24 weeks to about 48 weeks. The time period may be different for different HCV genotypes, e.g., about 24 weeks for patients infected with HCV genotype 2 or 3, or about 48 weeks for patients infected with HCV genotype 1.

A person suffering from HCV infection, in particular, chronic HCV infection, may exhibit one or more of the following signs or symptoms:

(a) elevated ALT;

(b) positive test for anti-HCV antibodies;

(c) presence of HCV as demonstrated by a positive test for HCV-RNA;

(d) clinical stigmata of chronic liver disease; or (e) hepatocellular damage.

Such criteria may not only be used to diagnose HCV, but can be used to evaluate a patient's response to drug treatment.

Elevated serum alanine aminotransferase (ALT) and aspartate aminotransferase (AST) are known to occur in uncontrolled HCV, and a complete response to treatment is generally defined as the normalization of these serum enzymes, particularly ALT. See Davis et al., *New Eng J Med*, Vol. 321, pp. 1501-1506 (1989). ALT is an enzyme whose concentration in blood is increased when liver cell function is impaired, e.g., due to HCV infection. Interferon causes synthesis of the enzyme 2',5'-oligoadenylate synthetase (2'5'OAS), which in turn, results in the degradation of the viral mRNA. See Houglum, *Clin Pharmacol*, Vol. 2, pp. 20-28 (1983). Increases in serum levels of the 2'5'OAS coincide with decrease in ALT levels.

In order to follow the course of HCV replication in subjects in response to drug treatment, HCV RNA may be measured in serum samples by, e.g., a nested polymerase chain reaction assay that uses two sets of primers derived from the N53 and N54 non-structural gene regions of the HCV genome. See Farci et al., *New Eng J Med*, Vol. 325, pp. 98-104 (1991); and Ulrich et al., *J Clin Invest*, Vol. 86, pp. 1609-1614 (1990).

Histological examination of liver biopsy samples may be used as a second criteria for evaluation. See, e.g., Knodell et al., *Hepatology*, Vol. 1, pp. 431-435 (1981), whose Histological Activity Index (portal inflammation, piecemeal or bridging necrosis, lobular injury and fibrosis) provides a scoring method for disease activity.

In the practice of the invention, the cyclosporin A or the cyclosporin A derivative is administered in association with the conjugate of interferon to a water-soluble polymer to a mammal, in particular, a human patient, exhibiting one of more of the above signs or symptoms in an amount and for a period of time sufficient to eliminate or at least alleviate one or more of the above-mentioned signs or symptoms. The course of the disease and its response to drug treatments may be followed by clinical examination and laboratory findings. The effectiveness of the therapy of the invention may be determined by the extent to which the previously described signs and symptoms of (chronic) HCV are alleviated and the extent to which the normal side effects of interferon, i.e., flu-like symptoms, such as fever, headache, chills, myalgia, fatigue, etc.; and central nervous system related symptoms, such as depression, paresthesia, impaired concentration, etc., are eliminated or substantially reduced.

The efficacy and safety of cyclosporin A administered in combination with pegylated-interferon can, e.g., be demonstrated by measuring the viral load (HCV-RNA), the serum ALT and AST and standard safety parameters, e.g., other liver function tests, blood cell count and biochemistry, at H0, H8, H12, H24, D2, D5, D7, D14, D21, D28 (where H is hour, D is day, 0 is time of first administration of treatment) in sequential cohort, multiple ascending dose design.

For example, Neoral® (cyclosporine capsules and cyclosporine oral solution) is given alone or/and in concomitance with pegylated interferon at doses from 3-5 mg/kg/day given in two to up to four doses.

Suitable patients are patients who are infected by HCV and present with abnormal liver function tests, especially abnormal ALTs. Preferably, they are "naïve" patients, i.e., none of them will already have received any kind of anti-viral treatment against HCV (interferon and or ribavirin).

In another aspect, Neoral® (cyclosporine capsules and cyclosporine oral solution) could be given to patients who have failed to respond to a treatment combining interferon or pegylated interferon with or without ribavirin.

In yet another aspect, the combination of pegylated interferon and Neoral® (cyclosporine capsules and cyclosporine oral solution) to the standard combination of pegylated interferon and ribavirin is compared. The assessment criteria will be a sustained virological response 48 weeks after the end of a 24-week (HCV genotype 2-3) or 48-week (HCV genotype 1) treatment. Treatment is conducted in naïve or refractory patients.

In another aspect, treatment is conducted in patients who fail to respond to a treatment combining pegylated interferon (or interferon) and ribavirin. The treatment regimen compares the rate of virological response obtained by adding Neoral® (cyclosporine capsules and cyclosporine oral solution) to the combination of pegylated interferon and Ribavirin.

We claim:

1. A method of treating a patient having a hepatitis C (HCV) infection, comprising administering to said patient a cyclosporin A or a cyclosporin A derivative in association with a conjugate of an interferon to a water-soluble polymer, in combination with ribavirin, wherein the patient has not previously responded to treatment of the HCV infection with an interferon or a pegylated interferon in combination with ribavirin.

2. The method according to claim 1. wherein HCV-RNA is measured in a serum sample from the patient following treatment with the cyclosporin A or the cyclosporin A derivative in association with the conjugate of interferon to the water soluble polymer, and wherein said HCV-RNA is detectably lowered.

3. The method according to claim 1, wherein said patient has chronic HCV.

4. The method according to claim 1, wherein the conjugate of interferon to the water-soluble polymer is a pegylated interferon.

5. The method according to claim 4, wherein the pegylated interferon is selected from the group consisting of pegylated consensus interferon, pegylated interferon alfa-2a and pegylated interferon alfa-2b.

6. The method according to claim 5, wherein the pegylated interferon is pegylated interferon alfa-2a or pegylated interferon alfa-2b.

7. The method according to claim 6, wherein the cyclosporin A is in a microemulsion pre-concentrate.

8. The method according to claim 1, wherein the cyclosporin A is administered in divided doses, two to four doses per day, resulting in a total dosage of about from 2-15 mg/kg/day.

9. The method according to claim 4, wherein the pegylated interferon is administered parenterally one to three times per week.

10. The method according to claim 1, wherein the duration of treatment is from about 20 weeks to about 100 weeks.

11. The method according to claim 1, wherein the patient is infected with HCV genotype 1, 2, or 3.

12. The method according to claim 11, wherein the HCV is of genotype 1.

13. The method according to claim 11, wherein the HCV is of genotype 2 or 3.

14. The method according to claim 1, wherein the patient has undergone a liver transplant before the treatment of HCV.

15. The method according claim 10, wherein the duration of the treatment is from about 24 to about 72 weeks.

16. The method according claim 15, wherein the duration of the treatment is from about 24 to 48 weeks.

* * * * *